United States Patent [19]

Pagé et al.

[11] Patent Number: 5,561,055
[45] Date of Patent: Oct. 1, 1996

[54] **BACTERIAL MASS PRODUCTION OF TAXANES WITH *ERWINIA***

[75] Inventors: Michel Pagé, Charlesbourg; Nathalie Landry, St-Jean-Chrysostome, both of Canada

[73] Assignee: BCM Developpement Inc., Charlesbourg, Canada

[21] Appl. No.: 436,006

[22] Filed: May 5, 1995

[51] Int. Cl.$^6$ ............................... C12N 1/20; C12P 17/02
[52] U.S. Cl. ......................... 435/252.1; 435/123; 435/34; 549/510; 549/511
[58] Field of Search ................................ 435/252.1, 123, 435/34; 549/510, 511

[56] References Cited

U.S. PATENT DOCUMENTS 5,322,779  6/1994  Strobel .................................. 435/123

OTHER PUBLICATIONS

Wani M C et al., 1971, *J. Am. Chem. Soc.*, 93:2325–2327.
McGuire W P et al., 1989, *Ann. Intl. Med.*, 111:273–279.
Holmes F A et al., 1991, *J. Natl. Cancer Inst.*, 83:1797–1805.
Murphy W K et al., 1992, Phase II study of Taxol (NCS 125973) in patients with non–small–cell lung cancer (NSCLC), *Proc. ASCO II (abstrc.)*:294.
Forastiere AA et al., Sep. 23–24, 1992, *Proceedings of the Second National Cancer Institute Workshop on Taxol and Taxus (abstrc.)*, Alexandria, VA:181–184.
B. Pagé et al., 1993, *Intl. J. of Oncology*, 3:473–476.
National Cancer Institute: *NCI Annual Report to the Food and Administration*: Taxol (IND 22850, NSC 125973), Bethesda, MD: NCI 1994.

*Primary Examiner*—Irene Marx
*Attorney, Agent, or Firm*—France Côté

[57] ABSTRACT

The present invention relates to a biologically pure culture of a novel bacteria of genus Erwinia, which is isolated from *Taxus canadensis*, and wherein said bacteria of genus Erwinia is characterized by the production of paclitaxel and related taxanes in a fermentative or respiratory type of metabolism from simple semi-synthetic or synthetic culture media. Also, the present invention relates to a method of bacterial mass production of paclitaxel and related taxanes which comprises the steps of: a) culturing the bacteria of genus Erwinia of the present invention in a growth-supporting nutrient medium capable of promoting growth and reproduction of said bacteria, and wherein said culturing is effected for a time sufficient to allow production of paclitaxel and related taxanes; and b) isolating said produced paclitaxel and related taxanes from said culturing medium of step a).

3 Claims, 9 Drawing Sheets

BACTERIAL MASS PRODUCTION OF TAXANES WITH *ERWINIA*

BACKGROUND OF THE INVENTION (a) Field of the Invention

The present invention relates to the use of a novel bacteria of genus Erwinia, referred to as *Erwinia taxi*, isolated from *Taxus canadensis*, for the production of paclitaxel and related taxanes. There is disclosed the methods of isolation of this bacteria and the screening tests that were used to prove the production of paclitaxel by said bacteria.

(b) Description of Prior Art

Paclitaxel, also referred to as Taxol™, has been first identified in 1971 by Wani and collaborators (Wani MC et al., 1971, *J. Am. Chem. Soc.*, 93:2325–2327) following a screening program of plant extracts of the National Cancer Institute. This complex diterpene demonstrated cytotoxic activity against several cancer cell lines such as KB cells, mouse leukemia cells (Wani MC et al., 1971, *J. Am. Chem. Soc.*, 93:2325–2327), and against in vivo systems such as intraperitoneally implanted B16 murine melanoma and MX-1 mammary tumor xenografted in mice (National Cancer Institute: *NCI Annual Report to the Food and Drug Administration:* Taxol (IND 22850, NSC 125973), Bethesda, Md.: NCI 1989). Later, activity has also been reported against different types of cancer; platinum-refractory ovarian cancer (McGuire WP et al., 1989, *Ann. Intl. Med.*, 11:273–279), refractory ovarian cancer (Holmes FA et al., 1991, *J. Natl. Cancer Inst.*, 83:1797–1805), breast cancer, lung cancer (Murphy WK et al., 1992, Phase II study of Taxol (NCS 125973) in patients with non-small-cell lung cancer (NSCLC), *Proc. ASCO II (abstrc.)*:294), head and neck cancer (Forastiere AA et al., Sep. 23–24, 1992, Phase II trial on Taxol in head and neck cancer: An Eastern Cooperative Oncology Group Study, *Proceedings of the Second National Cancer Institute Workshop on Taxol and Taxus (abstrc.)*, Alexandria, Va.). Several phase III clinical trials began in 1992 and paclitaxel has been approved in December 1992 by the Food and Drug Administration. It is now being used in the treatment of some cancers, mainly ovarian cancer.

Paclitaxel differs from other cytotoxic drugs by its unique mechanism of action. It interferes with cell division by manipulating the molecular regulation of the cell cycle. Paclitaxel binds to tubulin, the major structural component of microtubules that are present in all eukaryotic cells. Those microtubules form the mitotic spindle in the G2/M phase of cell division. Unlike other antimitotic agents such as vinca alkaloids and colchicine, which inhibit the polymerization of tubulin, paclitaxel promotes this assembly of tubulin and stabilizes the resulting microtubules. Thus, the division of the cell in two equal daughter cells is interrupted. Microtubules also regulate cell shape, they anchor surface receptors in the plasma membrane, they are involved in motility and in the formation of channels in neurotransmitter secretion. Within the cell, a dynamic equilibrium exists between microtubules and their depolymerized tubulin dimers. Paclitaxel disrupts this equilibrium thus preventing the transition from Go/G1 through S phase which causes a lethal metaphase arrest.

Paclitaxel is presently commercialized by Bristol-Myers Squibb (BMS) and the supply of the drug is problematic. The substance is extracted from the bark of the slow-growing Pacific yew, *Taxus brevifolia*. Actually, 16 000 pounds of bark are necessary to produce 1 kg of paclitaxel. The low yield of the isolation of paclitaxel (0,016 g %) and the limited availability of the trees have forced the scientific community to find alternative sources of producing paclitaxel.

Among those alternative sources, total synthesis of the drug would be an interesting compromise. Total synthesis of paclitaxel has been achieved in 1994 by Nicolaou et al. (1994, *Nature*, 367:630–634). The process is somehow multi-stepped and the overall yield has made this approach economically unrealizable. Nevertheless, semisynthesis of paclitaxel from its natural precursor, 10-deacetylbaccatin III, is now possible. This precursor can be extracted from a renewable source: the needles and twigs of the European yew *Taxus baccata*.

Plant cell culture of taxus species is another approach explored by many scientists. This process is limited by the quantity of paclitaxel that can be produced and the length of incubation time required to yield paclitaxel levels comparable with those produced by the intact plant. Those reasons have made this method economically unrealizable.

In U.S. Pat. No. 5,322,779, Gary A. Strobel et al. disclosed a fungus isolated from the bark of a sample of *Taxus brevifolia* which is able to synthesize paclitaxel at a level of only 24–50 ng/L after 3 weeks of cultivation. The utilization of this fungus with a slow growth at an industrial level would require large volumes of culture and long periods of incubation in order to extract significant amounts of the drug, which reduce the profitability of the process. With a microorganism having a higher doubling time and a higher rate of metabolism, larger quantities of paclitaxel could be extracted in a short delay. Bacteria possess these characteristics of growth, specially fermentative microorganisms.

Plants are hosts of a variety of microbes including fungus and bacteria. It is known that some of these microbes are able to synthesize secondary plant compounds. So, some genetic material could be exchanged between the host and microorganisms. It would be highly suitable if a bacteria could be used for the production of paclitaxel. As mentioned earlier, bacteria have, in general, a high doubling time and can be easily grown. Therefore, it would become a non-expensive renewable source of paclitaxel that can be applied to the pharmaceutical industry.

It would be highly desirable to be provided with a bacteria for the mass production of paclitaxel and related taxanes.

SUMMARY OF THE INVENTION

One aim of the present invention is to provide a novel bacteria for the mass production of paclitaxel and related taxanes.

Another aim of the present invention is to provide for a method of bacterial mass production of paclitaxel and related taxanes which overcomes all the drawbacks of the prior art.

In accordance with the present invention there is provided a biologically pure culture of a novel bacteria of genus Erwinia, which is isolated from *Taxus canadensis*, and wherein said bacteria of genus Erwinia is characterized by the production of paclitaxel and related taxanes in a fermentative or respiratory type of metabolism from simple semi-synthetic or synthetic culture media.

In accordance with the present invention there is provided a method of bacterial mass production of paclitaxel and related taxanes which comprises the steps of:

a) culturing the novel bacteria of genus Erwinia of the present invention in a growth-supporting nutrient medium capable of promoting growth and reproduction of said bacteria, and wherein said culturing is effected for a time sufficient to allow production of paclitaxel and related taxanes; and b) isolating said produced paclitaxel and related taxanes from said culturing medium of step a).

In accordance with the present invention, microorganisms from a sample of *Taxus canadensis* were isolated, and tested for the production of paclitaxel.

There is disclosed the discovery and usage of a novel bacteria able to produce paclitaxel and related taxanes. There is also disclosed the methods of isolation of this microorganism, the screening tests that were used for the chemical evidence of the paclitaxel production and the characterization of the bacteria.

For the purpose of the present invention the following terms are defined below.

The term "paclitaxel and related taxanes" is intended to mean any paclitaxel derivatives which have retained the taxol-associated cytotoxic biological activity or are thought to be precursors in the synthesis of paclitaxel. Such paclitaxel and related taxanes may be selected from the group consisting of all the diterpenes isolated from *Taxus canadensis* including 10-deacetyl baccatin III, baccatin III, cephalomannine and 10-deacetylcephalomannine.

The term "taxol-associated cytotoxic biological activity" is intended to mean a cytotoxic activity which is sufficient to promote the assembly of tubulin and stabilizes the resulting microtubules of cancer cells causing the division of the cells in two equal daughter cells to be interrupted; and sufficient to cause a disruption in the dynamic equilibrium which exists between microtubules and their depolymerized tubulin dimers, thus preventing the transition from Go/G1 through S phase which causes a lethal metaphase arrest of cancer cells.

"Cancer cells" is intended to mean any cancer cells which include without limitation, ovarian, breast, lung, head and neck cancer cells.

The term "growth-supporting nutrient medium" is intended to mean any simple semi-synthetic culture media which includes, without limitation, glucose, sodium acetate, phenylalanine, soyeton (Difco), vitamins and minerals.

FIG. 9 illustrates the mass spectrometry of the substances eluted between 45 and 48 minutes on High Performance Liquid Chromatography (HPLC) from different extracts of bacteria STJ.EPI.H7 (*Erwinia taxi*).

DETAILED DESCRIPTION OF THE INVENTION

Plant are hosts of a variety of microorganisms. The relation between the plant and the microorganism can be saprophytic, parasitic, endophytic or symbiotic. Whatever the relation, there may be a genetic exchange between the species. *Taxus canadensis,* which grows in some regions of the province of Quebec, shows significant amounts of paclitaxel in needles and stems. Samples of *Taxus canadensis* from 7 regions of the province were chosen. The present invention describes the isolation of microorganisms from various regions of Quebec. A bacteria of the genus Erwinia, classified STJ.EPI.HT, was isolated from a *Taxus canadensis* sample, demonstrated paclitaxel-producing properties.

A preferred bacteria isolated from *Taxus canadensis* in accordance with the present invention, which allows for the mass production of paclitaxel and related taxanes, referred to as *Erwinia taxi,* has been deposited at the American Type Culture Collection (ATCC, 12301 Parklawn Drive, Rockville, Md. 20852 USA) on April 25, 1995 under deposit number ATCC 55669. This deposit is available to be public upon the grant of a patent to the assignee, BCM D ÉVELOPPEMENT Inc., disclosing same. The deposit is also available as required by Foreign Patent laws in countries wherein counterpart applications are filed.

Isolation of microorganisms

The plant was divided in 5 parts; needles, twigs, stems, bark and roots. Each part of the plant was verified for the production of paclitaxel.

The surface of every part is sterilized with 95% ethanol and then, cut in small pieces with a sterile blade. Pieces are homogenized in sterile water with a Polytron™ that has been sterilized also with ethanol 95%. The resulting mix is used to inoculate three different culture media; R2A agar (Difco), Sabouraud agar (Difco) and Brain Heart Infusion (BHI) broth (Difco). R2A agar is a minimal media used in the enumeration and cultivation of microorganism from drinking water. Sabouraud agar is used for the culture of fungus and BHI for the culture of fastidious microorganisms.

Every plate and tube were incubated at 22° C. and examined on a day-to-day basis. The morphology of each colony was meticulously noted and the bacteria were transferred on different media until a pure culture was obtained. A Gram coloration of every bacteria is done before the culture is frozen at −80° C. Fungus species were kept at room temperature in a slant tube of Sabouraud agar covered with mineral oil.

A total of 23 bacteria and 9 fungi were isolated from the taxus of the region of Quebec city. One bacteria isolated from *Taxus canadensis,* referred to as *Erwinia taxi,* isolated from the needles of the sample was fully characterized. Four other bacteria seem to be very promising, and are presently under investigation.

Primary screening of microorganisms

In order to verify the production of paclitaxel by microorganisms, each organism was cultured in one liter of a nutrient broth containing sugars, minerals, vitamins and supplemented with phenylalanine and sodium acetate because these substances are necessary for the metabolism of paclitaxel. Every culture was incubated at 22° C. for a minimum period of three days with constant shaking.

The culture was centrifuged and the pellet separated from the supernatant by decantation. To verify if paclitaxel was secreted in the culture medium or if it was confined within the cells, both were tested for the presence of the drug. Since paclitaxel is very hydrophobic and in order to concentrate each sample, an extraction with dichloromethane was performed. The pellet was diluted with one volume of dichloromethane. The same procedure was repeated for the supernatant. In the case of fungus, the pellet was first homogenized with a Polytron™. After appropriate shaking, organic fractions were collected and evaporated to dryness. Then, the residue of each extraction was dissolved in 500 μof methanol 0,1% acetic acid. So, for each microorganism, an extract for the pellet and one for the supernatant were produced.

a) The HPLC screening

Each extract was analyzed by High Performance Liquid Chromatography (HPLC). The HPLC system consisted of a Waters™ 625 LC pump and a Waters™ 996 photodiode array detector. Chromatography was performed with a phenyl column (5 μm particle size, 6 mm ×15 mm) with a guard module. The injection volume was 50 μl and the flow rate maintained at 1 ml/min. The following elution program was used:

0 to 20 min.: methanol:water:acetonitrile (20:65:15) ramped to methanol:water:acetonitrile (20:45:35)

20 to 50 min.: methanol:water:acetonitrile (20:45:35) ramped to methanol:water:acetonitrile (20:25:55)

50 to 60 min.: methanol:water:acetonitrile (20:25:55) ramped to methanol 100%

Figure 1:
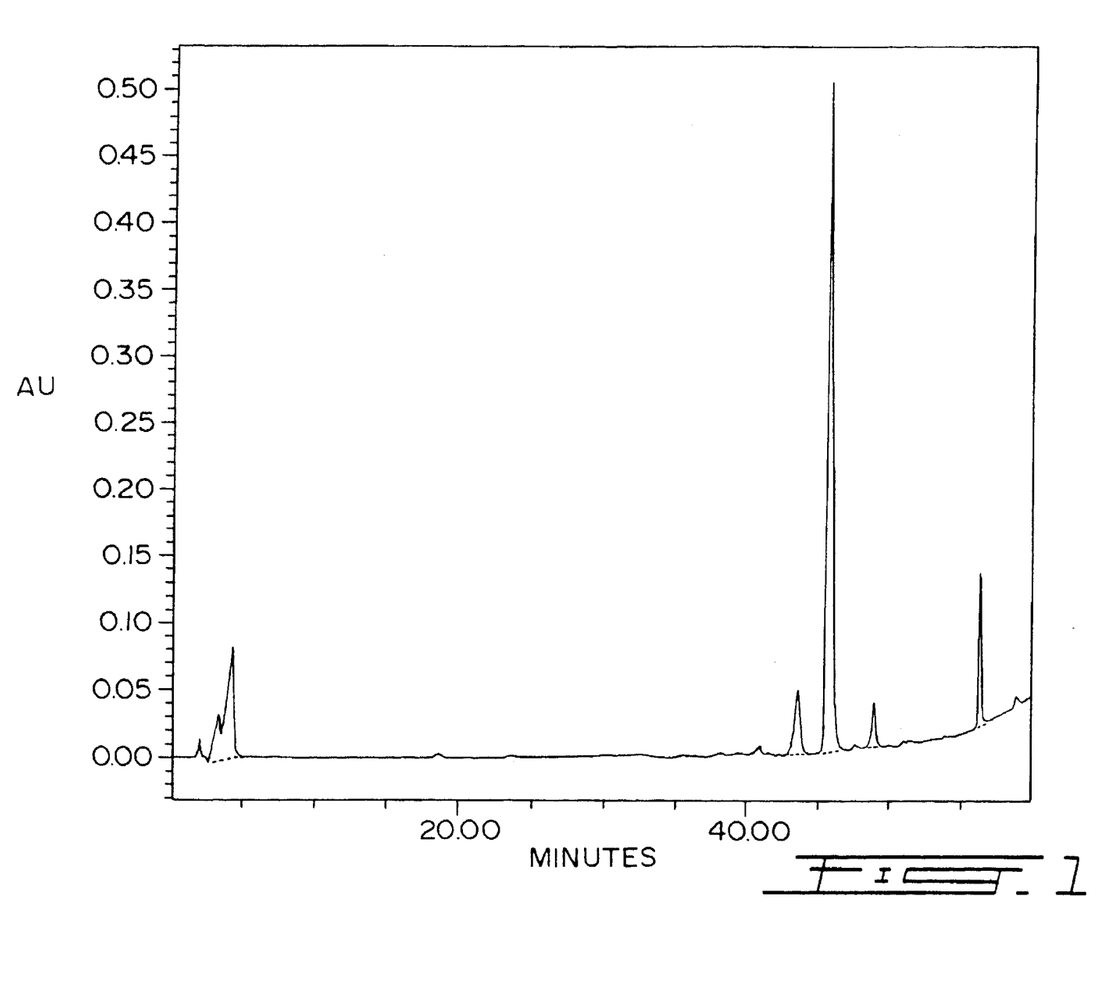
FIG. 1 shows the elution profile of a partially purified extract of *Taxus canadensis* obtained from Biolyse (Québec, Canada)
Figure 2:
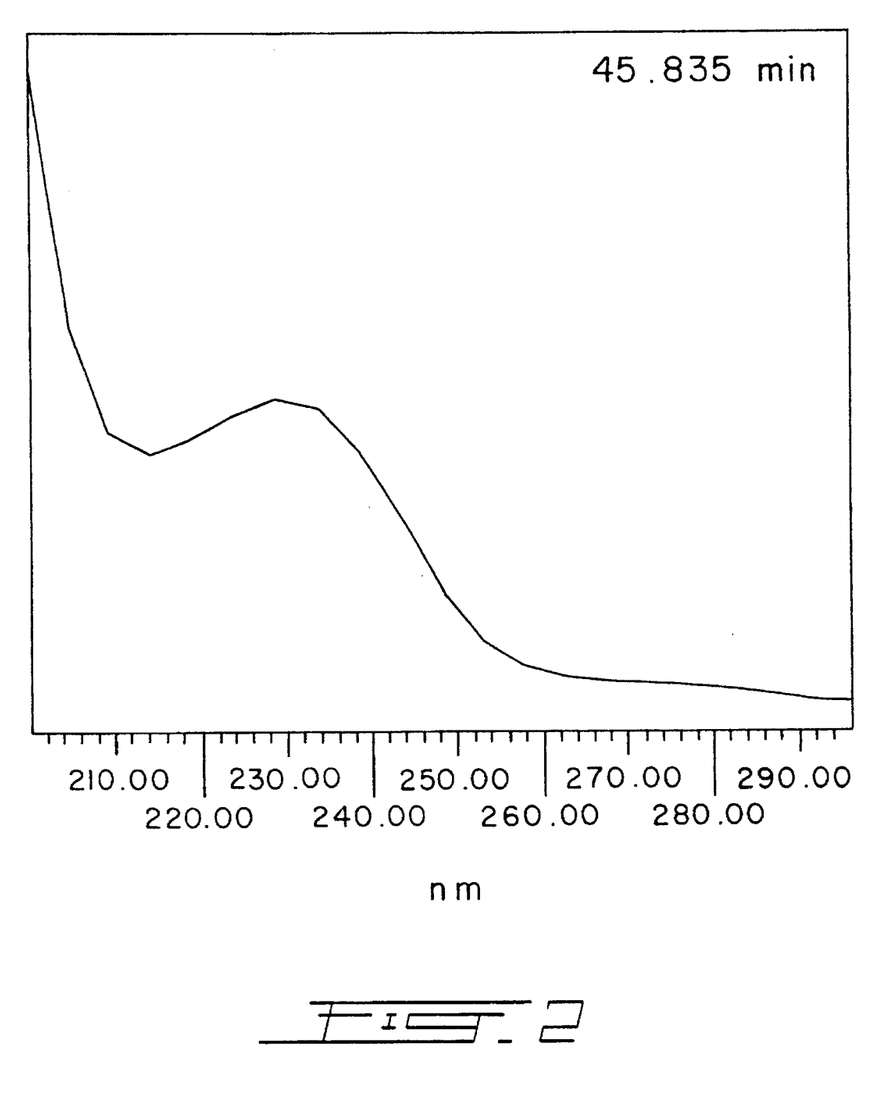
FIG. 2 shows the UV spectra of paclitaxel eluted at 45,835 min.

The UV spectra of taxanes shown in FIG. 2, specially the one of paclitaxel, are very characteristic with a maximum of absorption at 230 nm. The spectra and the elution time give a very good indication of the nature of substances produced by microorganisms.

Figure 3:
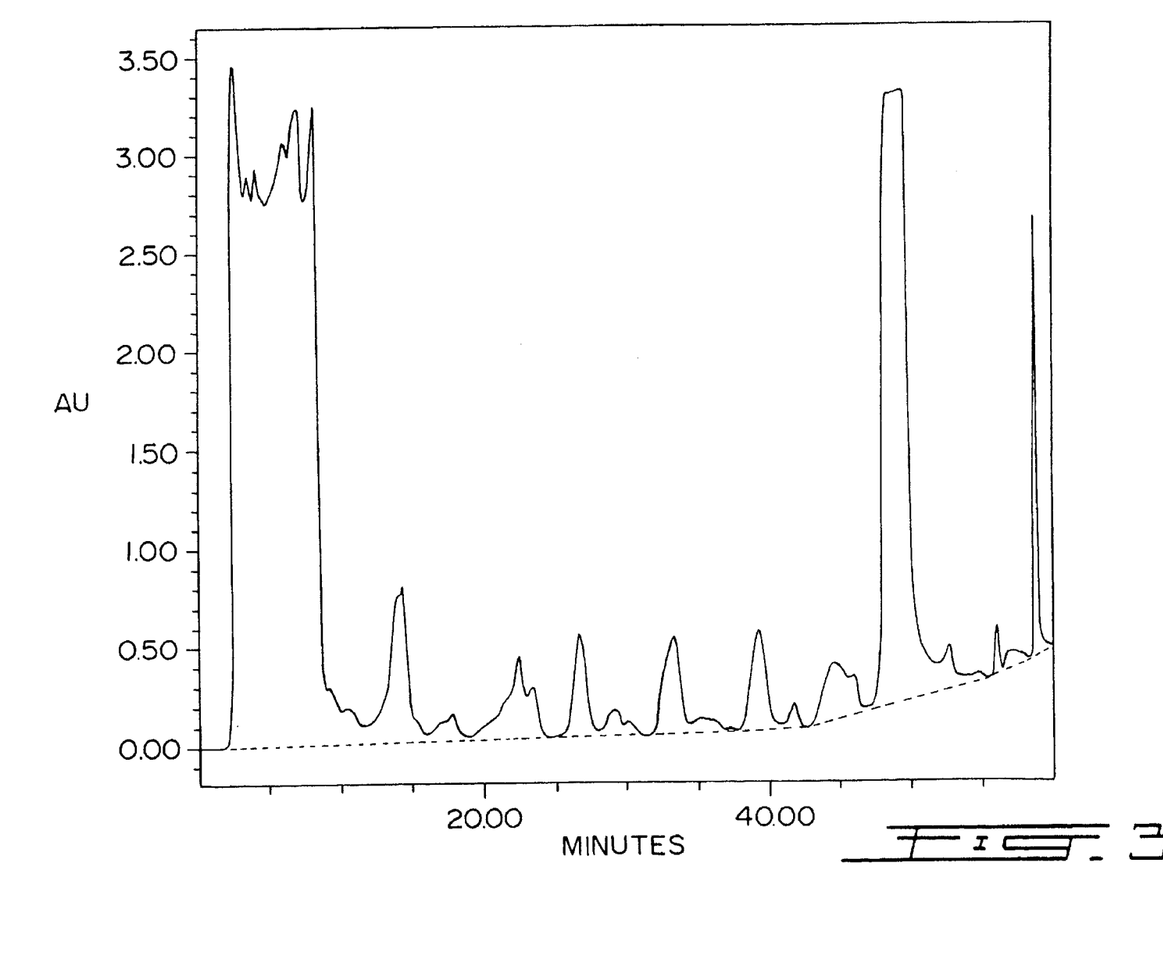
FIG. 3 shows the elution profile of a supernatant extract of the preferred bacteria referred to as STJ.EPI.H7 (*Erwinia taxi*)
Figure 4:
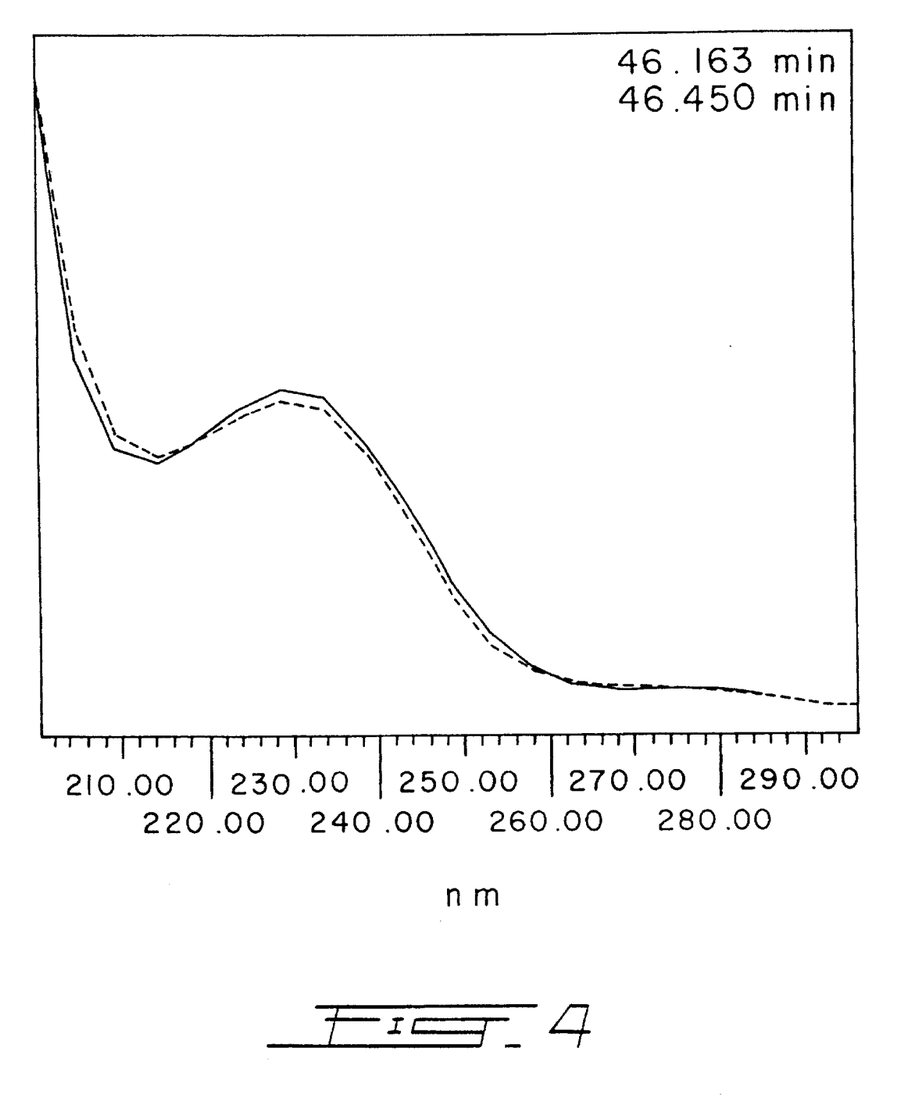
FIG. 4 the UV spectra of paclitaxel obtained from a partially purified extract of *Taxus canadensis* and of supernatant extract of the preferred bacteria referred to as STJ.EPI.H7 (*Erwinia taxi*)

The elution profile of a supernatant extract of bacteria *Erwinia taxi* (FIG. 3) and the UV spectra of paclitaxel from different sources (FIG. 4) clearly illustrate that a substance is produced by STJ.EPI.H7 which has the same retention time and the same UV spectra as paclitaxel.

b) Cytotoxicity on cancer cells

Figure 5:
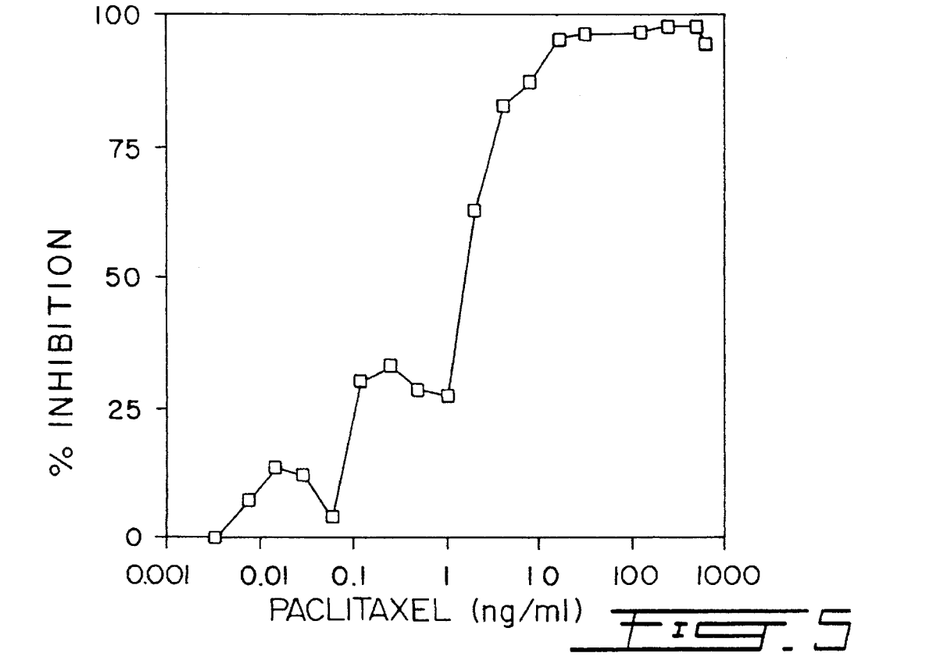
FIG. 5 illustrates the cytotoxicity of paclitaxel ATCC CRL-1572 cell line.
Figure 6:
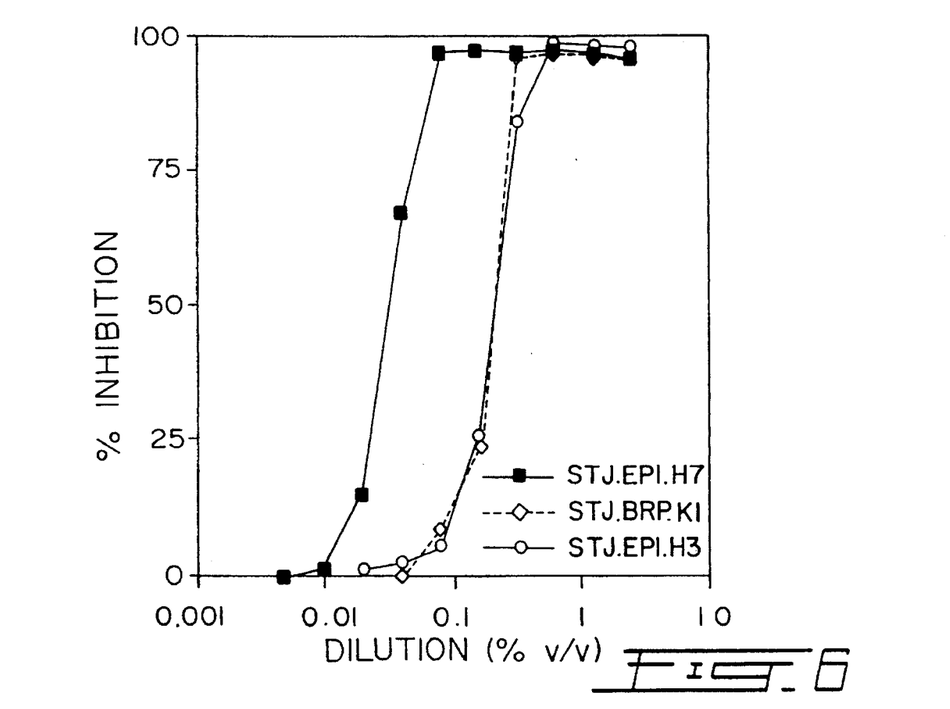
FIG. 6 shows the cytotoxicity of three different supernatant extracts of microorganisms isolated from a sample of *Taxus canadensis*.

An ovarian cancer cell line (ATCC accession number CRL-1572, Rockville, USA) was chosen for the investigation. Briefly, 2 000 cells/well of a 96wells microplate were inoculated. After 2 days, different dilutions of the drug were added in a volume of 100 μ. Three days later, the viability of cells was measured with ALAMAR™ blue (B. Pagé et al., 1993, *Intl. J. of Oncology*, 3:473–476). The ATCC CRL-1572 cell line is particularly sensitive to paclitaxel ($ID_{50}$ of 1 ng/ml) as shown in FIG. 5. Every microbial extracts have also been tested for their cytotoxicity on those cells FIG. 6 shows the cytotoxicity of three different supernatant extracts. This figure clearly demonstrates that a supernatant extract from bacteria *Erwinia taxi* is ten-fold more cytotoxic than other extracts.

Secondary screening of microorganisms

Further investigations required larger amounts of extracts. Cultures of 5 liters were produced and the production of extracts was effected as described above.

a) Flow cytometry

As mentioned earlier, paclitaxel causes an arrest of cells in the G2/M phase. In which phase, the cell possesses 2n chromosomes. The replication of DNA is a very precise mechanism and the division process of a population of cells can be evaluated by DNA staining. Propidium iodide, a fluorescent substance, binds to DNA in a constant ratio. So, the amount of fluorescence registered for a particular cell is directly proportional with its DNA content. One way to measure the fluorescence for each cell of a population is by flow cytometry. In this process, each cell passes in front of an argon laser at a wavelength of 488 nm. The flow cytometer can register up to 5 parameters: cell size (forward scattered), granularity (side scattered) and three different fluorescences (green, orange and red)

To perform this experiment, ATCC CRL-1572 cells were cultured in RPMI 1640 supplemented with 10% fetal calf serum. After an incubation of 2 days, the drug was added to the medium: paclitaxel (5 ng/ml) or 2,5–15 μl/ml of the preferred bacteria *Erwinia taxi* extract. Twenty hours later, cells were trypsinized and centrifuged, the supernatant discarded and nuclei were prepared as follow: the pellet was resuspended in 1 ml of PBS 0,01% Triton™ X-100 and incubated on ice for 15 minutes. Nuclei were centrifuged, the supernatant discarded and the pellet resuspended in 1 ml of FACS™ flow (Becton Dickinson). 50 μl of propidium iodide (1 mg/ml) were added and the cells were analyzed on a FACS™ Sort (Becton Dickinson).

Figure 7A:
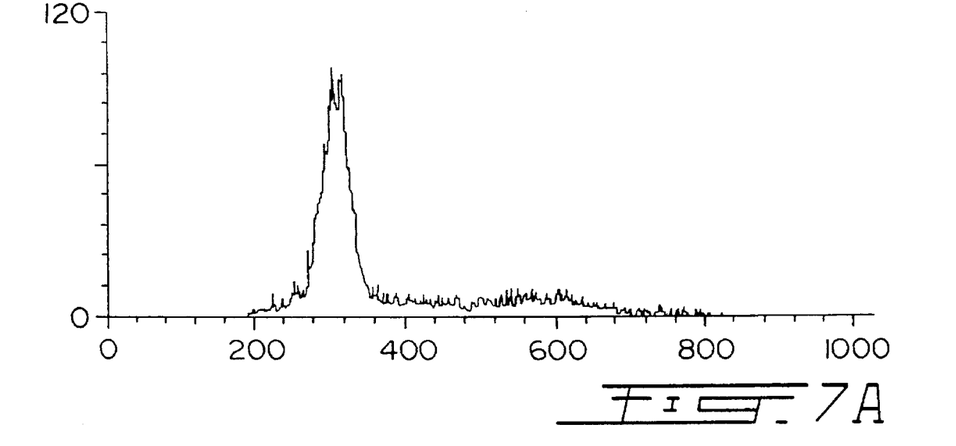
FIG. 7 shows a typical normal cell cycle compared with the cell cycle resulting of an incubation with paclitaxel or with an extract of bacteria STJ.EPI.H7 (*Erwinia taxi*)
Figure 7B:
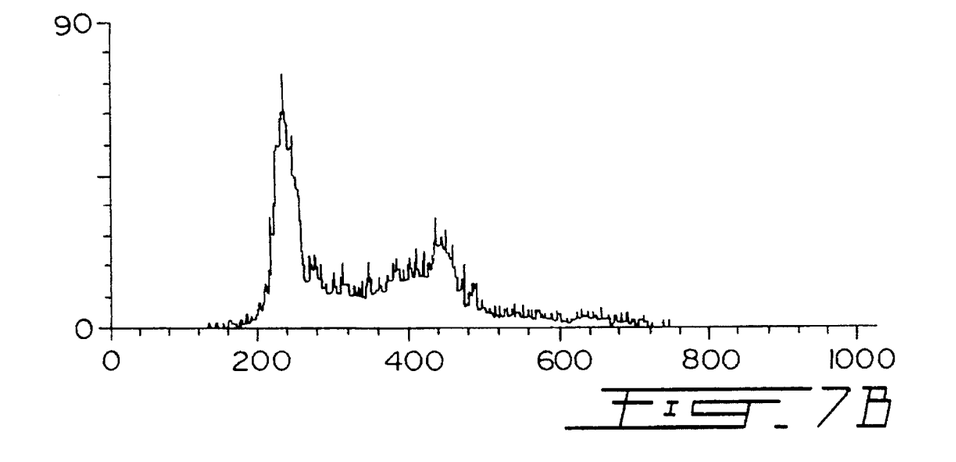
Figure 7C:
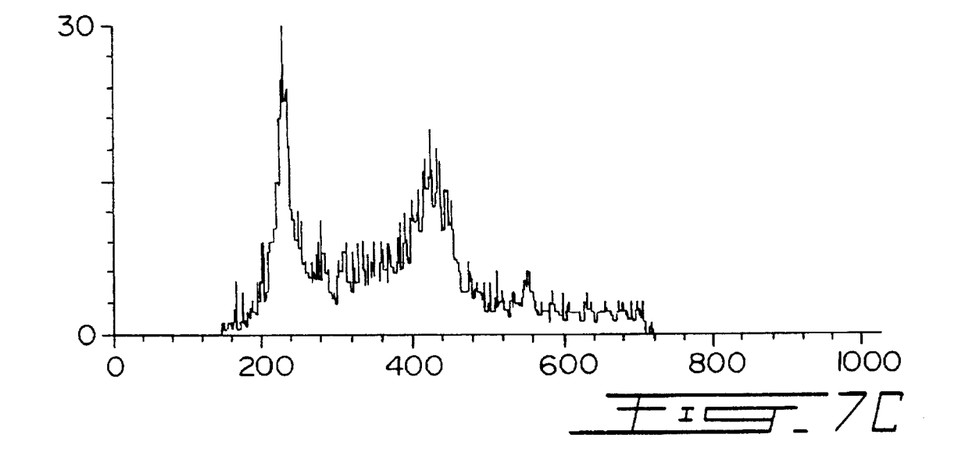

FIG. 7 shows a typical normal cycle compared with the cell cycle resulting of an incubation with paclitaxel or with an extract of *Taxus canadensis* bacteria *Erwinia taxi*. A statistical model can be applied to those results and the proportion of cells in the three different phases of the cellular cycle can be obtained. Table I summarized the statistics obtained from these samples. It clearly demonstrated that paclitaxel causes an accumulation of cells in S and G2/M phases and that a supernatant extract of bacteria *Erwinia taxi* acts in the same way.

TABLE 1

Statistics of the cell cycle of CRL-1572 cultured in different conditions

| Sample | Phase of cell cycle | | |
|---|---|---|---|
| | G0/G1 % of cells | S % of cells | G2/M % of cells |
| A-control | 81,9 | 9,3 | 8,8 |
| B-paclitaxel (5 ng/ml) | 39,6 | 39,1 | 21,4 |
| C-supernatant extract of STJ.EPI.H7 (2,5 μl/ml) | 21,4 | 54 | 24,6 | b) Purification of the substances produced by STJ.EPI.H7 and associated cytotoxicity A separation of the substances produced by *Erwinia taxi* was effected using HPLC. The same conditions as described above were used and 1 ml fractions were collected. Each fraction was evaporated to dryness and resuspended in 40 μl of methanol. 100 μl of different dilutions of the solution were added to the wells of the microtiter plate. Cell viability was measured three days later as described above.

Figure 8:
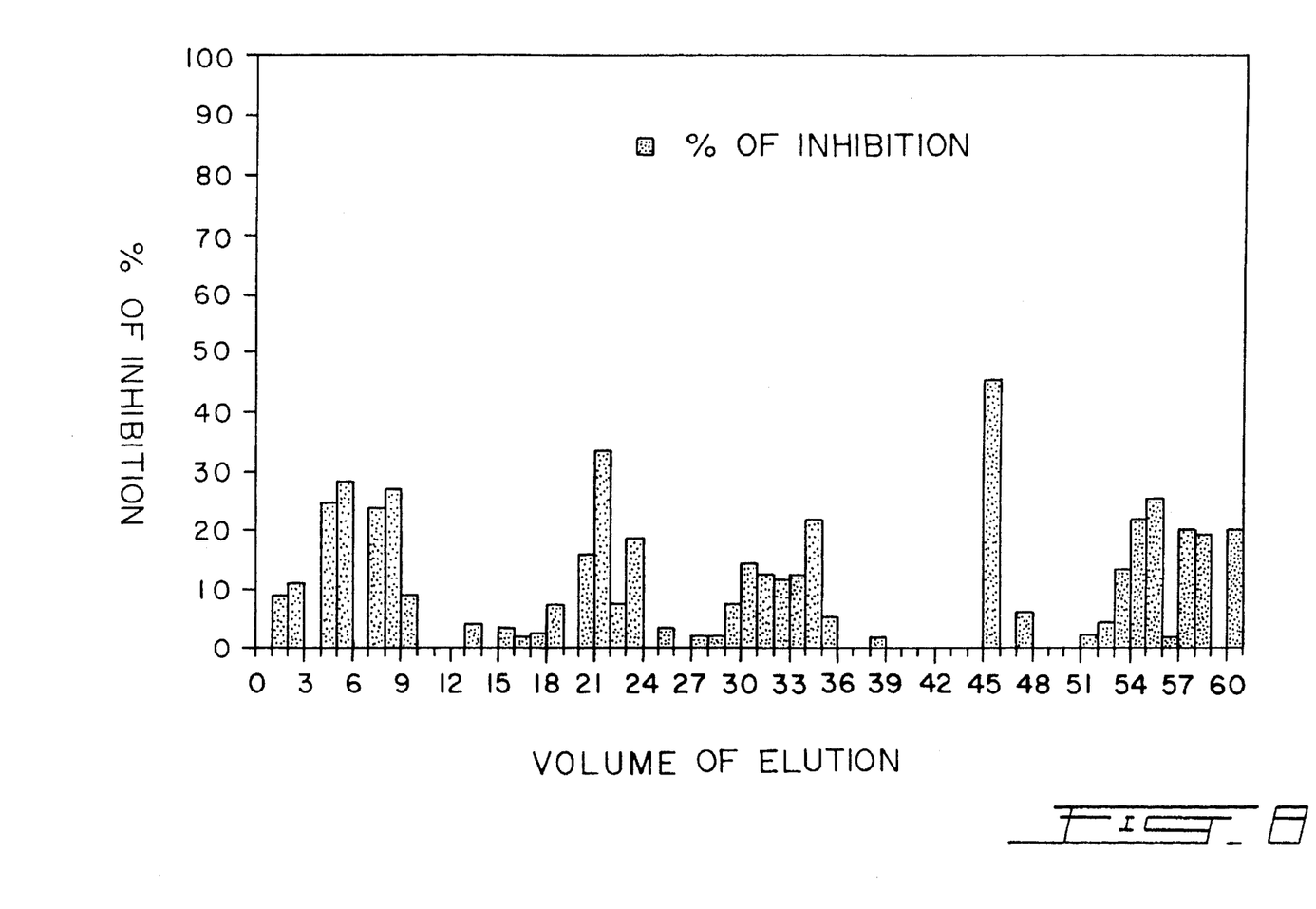
FIG. 8 shows the relative cytotoxicity of the fractions collected from the chromatography of a pellet extract of bacteria STJ.EPI.H7 (*Erwinia taxi*); and
Figure 9A:
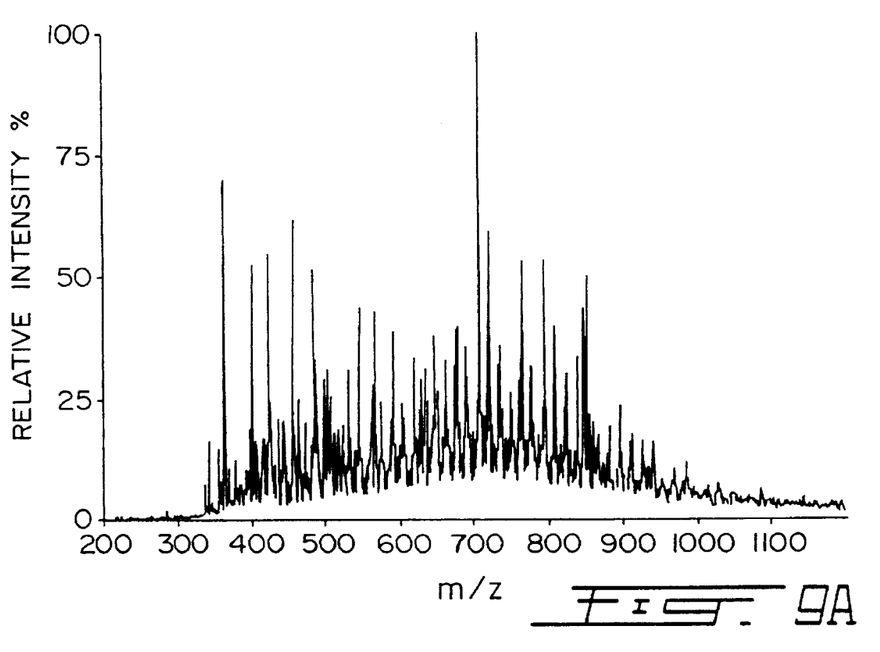
Figure 9B:
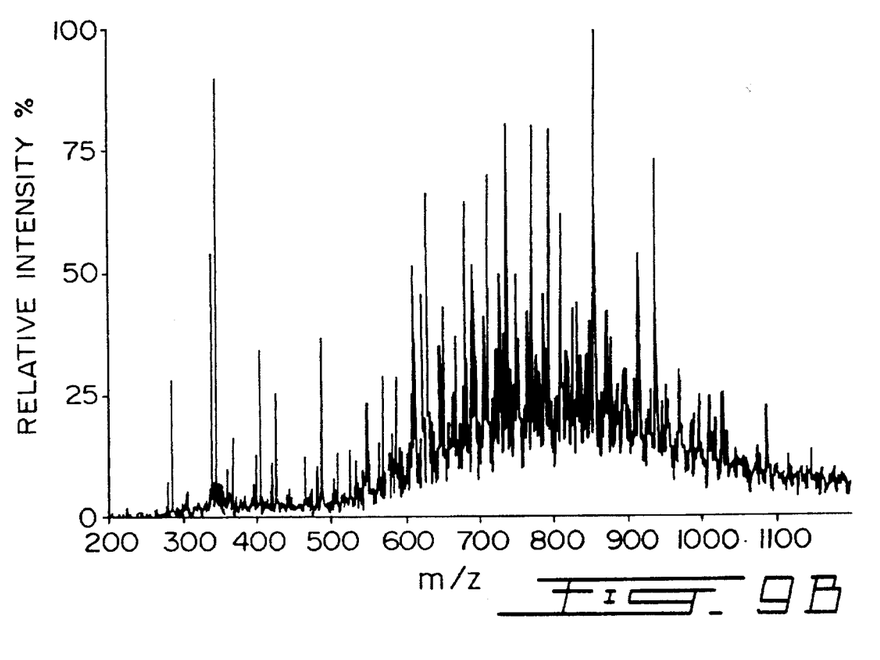
Figure 9C:
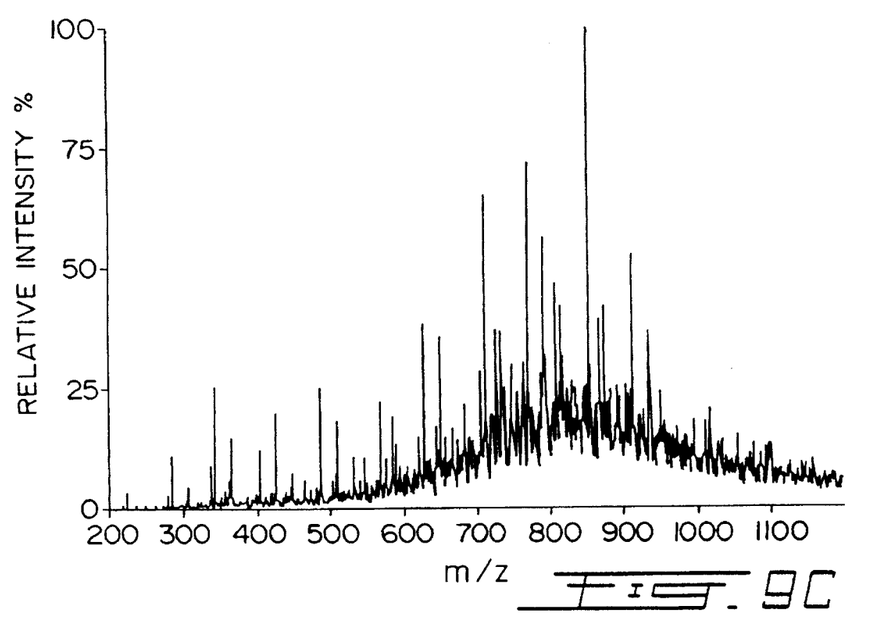
Figure 9D:
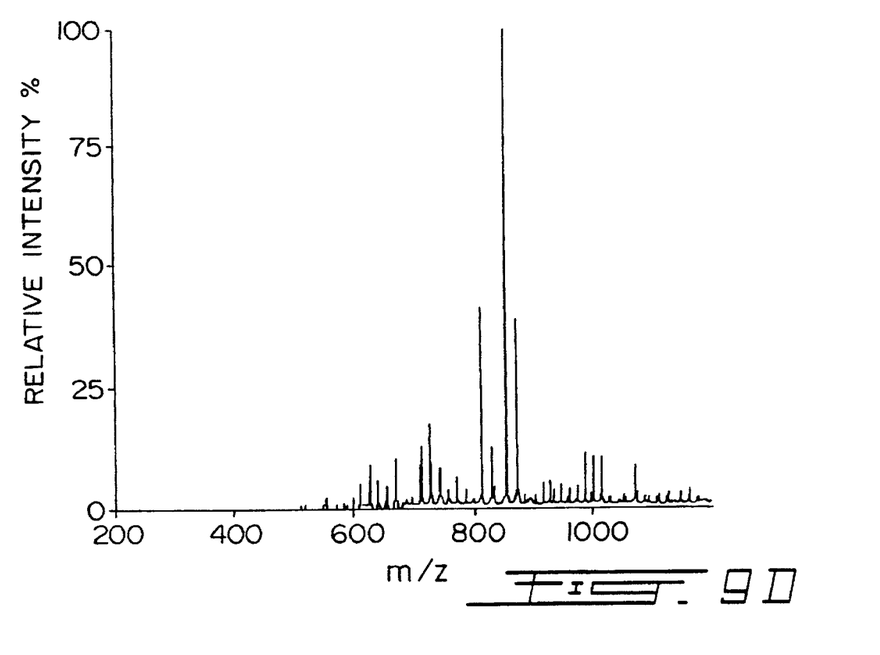

FIG. 8 shows the relative cytotoxicity of the fractions collected from the chromatography of a pellet extract of *Erwinia taxi.* The major cytotoxicity is associated with the substance eluted around 46 minutes and which substance corresponds to paclitaxel.

c) Mass spectrometry

Mass spectrometry of the substances eluted between 45 and 48 minutes from different extracts of bacteria STJ.EPI.H7 was performed. FIG. 9 shows the results. In every sample, a substance with a molecular weight (M.W.) of 853,5 daltons appears. The theoretical M.W. of paclitaxel is 854 daltons. Even if these extracts were partially purified, essentially the major substance obtained is paclitaxel.

Characterization of bacteria *Erwinia taxi*

The bacteria *Erwinia taxi* was isolated from the needles of a sample of *Taxus canadensis.* This bacteria is Gram negative or variable, but the ultrastructure of the cell is always negative. Cells are straight rods and the length of the cells change with the culture medium. On a medium containing glucose, cells are short rods, but on nutrient agar containing no sugar cells may be very long. Cells are motile but flagella has not been characterized. The catalase reaction is positive and the oxidase reaction negative. Indole test is also negative. Colonies are opaque, smooth, convex and are yellow to orange depending on the age of the culture. Colonies may also appear slimy when grown on an acidic medium. Metabolism can be either respiratory or fermentative. Tables 2 and 3 summarize the culture, physiological and biochemical characteristics of bacteria *Erwinia taxi.*

TABLE 2

Cultural, physiological and biochemical characteristics of bacteria Erwinia taxi

| CHARACTERISTIC | Erwinia taxi |
|---|---|
| Gram | – |
| Motility | + |
| Catalase | + |
| Growth on Mac Conkey | – |
| Growth at pH < 5 | + |
| Oxidase | – |
| Indole test | – |
| Starch hydrolysis | – |
| $H_2S$ production | – |

TABLE 3

Metabolism of bacteria Erwinia taxi

| | Metabolism | | | |
|---|---|---|---|---|
| | Respiratory | | Fermentative | |
| Substrate | Growth | Acid production | Growth | Acid production |
| Glucose | + | + | + | + |
| Fructose | weak | – | + | + |
| Lactose | weak | – | + | + |
| Mannose | weak | – | + | + |
| Galactose | + | + | + | + |
| Maltose | + | weak | + | + |
| Xylose | + | moderate | + | moderate |
| Ribose | + | – | + | weak |
| Inositol | weak | – | weak | weak |
| Sorbitol | weak | – | weak | weak |
| Glycerol | moderate | – | weak | weak |

From these results, it can be assumed that the bacteria of the present invention is of the genus Erwinia. The species of this genus are usually associated with plants as pathogens, saprophytes, or as constituents of the epiphytic flora. *Erwinia taxi* shows a lot of similarities with this genus, even if there is a lot of heterogeneity between species of Erwinia. Particularities of this genus include motility, a negative Gram coloration, a positive catalase reaction, a negative oxidase reaction, and a facultative anaerobic metabolism. Unfortunately, we cannot associate the bacteria with a particular species within the genus Erwinia, but *Erwinia taxi* seems to be a new member of the Herbicola group.

The present invention will be more readily understood by referring to the following example which is given to illustrate the invention rather than to limit its scope.

EXAMPLE I

Mass production of paclitaxel

A colony of a pure culture of *Erwinia taxi* is used to inoculate 5 ml of the semi-synthetic culture medium. The broth is incubated 2–3 days with constant shaking (90 rpm) at 22° C. This 5 ml is then transferred into 5 liters of the same culture medium. The resulting broth is incubated as described above. The bacteria can either be cultured in a fermentative or respiratory mode.

After 4–5 days of incubation, or after the maximum cell density is reached, the cell pellet is separated from the supernatant by ultrafiltration on a Minitan™ system from Millipore Corporation. Hydrophobic compounds are then extracted from the pellet and the supernatant by partition with one volume of dichloromethane. Each organic fraction is evaporated to dryness, and the residue is solubilized in a minimal amount of methanol containing 0.1% acetic acid, typically about 500 µl to about 1–2 ml.

Paclitaxel and related taxanes are further purified by HPLC on a phenyl column. Typically, up to 400 µl of the methanolic solution are injected and fractions of 0.5 ml to 1 ml are collected. The elution program described previously was used. Fractions containing paclitaxel or related taxanes are evaporated to dryness.

Using this method, from 200 ng to 1 µg of paclitaxel per liter of culture medium within 4–5 days were purified.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A biologically pure culture of a strain *Erwinia taxi* which produces taxanes in a recoverable amount in an aqueous nutrient medium containing assimilable sources of carbon, nitrogen and inorganic substances, having all of the identifying characteristics of *Erwinia taxi* strain ATCC 55669.

2. The culture of claim 1 which is *Erwinia taxi* strain ATCC 55669.

3. A method of production of taxanes which comprises the steps of a) culturing *Erwinia taxi* ATCC 55669 in an aqueous nutrient medium containing assimilable sources of carbon, nitrogen and inorganic substances for a time sufficient to allow production of taxanes; and b) isolating said produced taxanes from said nutrient medium.

* * * * *